(12) United States Patent
Liland et al.

(10) Patent No.: US 7,802,991 B2
(45) Date of Patent: Sep. 28, 2010

(54) MASK SEAL TRAINER

(75) Inventors: Frode Liland, Stavanger (NO); Børge Lund, Hundvåg (NO)

(73) Assignee: Laerdal Medical AS (NO)

( * ) Notice: Subject to any disclaimer, the term of this patent is extended or adjusted under 35 U.S.C. 154(b) by 924 days.

(21) Appl. No.: 10/595,258

(22) PCT Filed: Oct. 1, 2004

(86) PCT No.: PCT/NO2004/000293

§ 371 (c)(1), (2), (4) Date: Dec. 16, 2006

(87) PCT Pub. No.: WO2005/030334

PCT Pub. Date: Apr. 7, 2005

(65) Prior Publication Data

US 2007/0089747 A1    Apr. 26, 2007

(30) Foreign Application Priority Data

Oct. 1, 2003    (NO) .................................. 20034391

(51) Int. Cl.
*G09B 23/28*    (2006.01)
(52) U.S. Cl. ..................................... 434/265
(58) Field of Classification Search ................. 434/262, 434/265, 267, 268, 270, 272
See application file for complete search history.

(56) References Cited

U.S. PATENT DOCUMENTS

| | | | |
|---|---|---|---|
| 3,274,705 A * | 9/1966 | Breakspear ................ 434/265 |
| 4,723,435 A * | 2/1988 | Huszczuk ................... 73/1.05 |
| 4,878,388 A * | 11/1989 | Loughlin et al. ........... 73/866.4 |
| 4,971,051 A | 11/1990 | Toffolon et al. |
| 5,423,685 A * | 6/1995 | Adamson et al. ............ 434/265 |
| 5,557,049 A * | 9/1996 | Ratner ........................ 73/715 |
| 5,580,255 A * | 12/1996 | Flynn ......................... 434/265 |
| 5,823,787 A * | 10/1998 | Gonzalez et al. ........... 434/265 |
| 6,296,490 B1 * | 10/2001 | Bowden ..................... 434/265 |

FOREIGN PATENT DOCUMENTS

GB    649689 A    1/1951

(Continued)

OTHER PUBLICATIONS

"Fundamentals BLS for Healthcare Providers", American Heart Association, Fighting Heart Disease and Stroke, published as recently as 2001, 3 pages.

(Continued)

*Primary Examiner*—Kurt Fernstrom
(74) *Attorney, Agent, or Firm*—Brooks Kushman P.C.

(57) ABSTRACT

A device for practicing mask ventilation, comprising a first passage and a second passage. The first passage is designed to provide communication between a source of air and the interior of a patient mask. The patient mask is designed for placement over a person's mouth and/or nose. The second passage is designed to provide communication between the air source and a back pressure means. The back pressure means is adapted to simulate the resistance of a human airway. The device can also comprise a third passage designed to provide communication between a breathing person and the surroundings. The passages may be formed in one integrated adapter to be placed between a patient valve and the mask.

18 Claims, 6 Drawing Sheets

FOREIGN PATENT DOCUMENTS

| | | |
|---|---|---|
| GB | 1040291 A | 8/1966 |
| WO | 002611 A | 1/2000 |

OTHER PUBLICATIONS

John Emory Campbell, MD, FACEP, BRADY 2000, "Basic Trauma Life Support", for Paramedics and Other Advanced Providers, fith edition, 25th anniversary edition, 66 Chapter 4, publication date unknown, 3 pages.

Laerdal, Products Catalogue, Lifesaving products for today's Good Samaritans, publication date unknown 2 pages.

Laerdal, Helping save lives, 1994, 2 pages.

* cited by examiner

MASK SEAL TRAINER

The present invention regards a means of practicing mask ventilation comprising a first passage and a second passage, said first passage being designed to provide communication between a source of air and the interior of a patient mask, said patient mask being designed to be placed over the nose and/or mouth of a person.

Today, the practicing of mask ventilation mainly takes place by use of a manikin. These manikins are excellent for providing basic training for treating personnel, as they allow air to be blown or otherwise forced into the manikin's "lungs", e.g. by use of mouth-to-mouth resuscitation or by use of bag-mask ventilation. Generally, the manikins are robust and will stand up to any mistakes made in the treatment.

However, these manikins suffer from a common problem; they are not humans with the natural variations in the shape of the face, hair growth and distinctive features that occur in humans. The chin, cheeks and skin of humans may vary greatly. Also, the manikins will be static, while humans may exhibit a varying degree of mobility of the head, softness of facial features, skin type, layer of fat etc.

After completing the hospital training program using manikins, a fresh rescuer will be sent out into the field and/or will be allowed to practice in hospitals. Here, he or she will be allowed to spend some time observing experienced rescuers at work. After also completing this phase, he or she will more or less be thrown in at the deep end of the difficult work of saving lives. From having practiced on manikins, the rescuer will now join in trying to save the life of a real person. This person will not behave in the same way as a manikin. One of the greatest problems is the fact that the person may have a facial shape or facial hair that makes it difficult to achieve a good seal between the patient mask (breathing mask) and the face. The patient may have dentures that have fallen out or have to be removed, and which make the area around the mouth less firm and difficult to seal against.

The result of a poor mask seal is a reduced supply of air to the patient. Thus the chances of successful resuscitation are diminished.

Several studies have been carried out, looking at the training of rescuers. The following appears in the text book "Fundamentals of BLS for Healthcare Providers", American Heart Association, published as recently as 2001: "Several studies have shown that rescuers in training often adequate rescue breaths to manikins because they are unskilled in use of the device. A lone rescuer may have difficulty obtaining an airtight seal to the face while squeezing the bag and maintaining an open airway."

The text book "Basic Trauma Life Support", Brady 2000, states the following: "Mask leakage is a serious problem, decreasing the volume delivered to the oropharynx by sometimes 40% or more."

Several other textbook series deal with the same problem. Generally, they describe the difficulties of obtaining sufficient practice in the psychomotor skills, especially as there is a limit to how much one can practice on real persons. It is also possible to ventilate directly on volunteers who must then try not to use their own breathing muscles during the training and instead let the air from the bag flow into their lungs. This is a very unpleasant situation for the volunteer. In addition the bag will become contaminated unless the bag is fitted with filters.

GB 2339392 describes a mask for resuscitation. It has an outlet pipe containing a ball. The movement of the ball may be supervised to check the gas supply to the patient or the expiration of the patient. This mask is not intended for training. The ball provides a small resistance to the air flow, but this resistance should be as little as possible in order to let the air pass as unhindered as possible. Consequently, the ball does not provide a resistance that simulates the resistance of a human lung, and thus this mask is not suitable for training purposes. The resistance will be too low to build up sufficient pressure within the mask and there may be an insufficient air sealing between the mask and the patient without the rescuer noticing this.

The present invention proposes to remedy the above deficiency in the rescuer training program by practicing mask sealing on healthy living persons. As an example, this may entail a volunteer holding his breath for a period while the rescuer practices achieving a good mask seal.

This is achieved by a device of the invention wherein said second passage is designed to provide communication between the air source and a back pressure means, said back pressure means simulating the resistance of a human airway.

As the volunteer must hold his breath during the practicing (in order to avoid air from the air reservoir being forced into his lungs), the period of such training is somewhat reduced.

Thus a preferred embodiment of the present invention aims to provide equipment which will make it possible to practice on live persons while allowing the volunteer to breathe as required without interrupting the training.

This is achieved by providing communication between a breathing person and the surroundings.

This provides a satisfactory training situation for the rescuer, who is able to force air from the reservoir to the interior of the mask via the first passage, thereby being able to check the sealing of the mask against the area around the patient's nose and/or mouth, and the discomfort experienced by the volunteer is reduced, as he is allowed to breathe via the second passage independently of the inflations via the first passage.

Preferably, the device has indicator means that indicate air flow through said first passage to facilitate control of the air flow.

Preferably, the indicator is a damper biased in a crosswise position in said first passage, which facilitates visual control and is convenient to implement.

In a preferred embodiment back pressure means is an artificial lung, which upon filling will indicate the volume delivered from said air source. This enables the use of a conventional test lung.

In an alternative embodiment the back pressure means is a restriction. This is a low cost and in many cases sufficient back pressure means.

In a preferred embodiment the first, second and third passages are formed in an integrated adapter designed to be placed between a patient valve and the mask. This enables the use of a conventional mask and a conventional patient valve.

In an alternative embodiment the first and second passages are formed in an integrated adapter, and said third passage is formed in a separate unit. This facilitates the construction of a training device for children.

In a further alternative embodiment the third passage extends through the wall of the mask at a distance from the connection of the mask to said first passage. This enables conventional resuscitating equipment to be used directly on a special training mask.

Preferably, the third passage communicates with both the breathing person's mouth and nose. This removes the need for closing the person's nose before training.

Preferably, the resistance provided by the back pressure means is between 5 and 40 cm $H_2O$/l/s, e.g., about 20 $H_2O$/l/s, which complies well with the resistance of human airways.

Preferably, the back pressure means has a compliance simulating the compliance of a human airway the compliance being between 0.01 and 0.15 l/cm $H_2O$, e.g., about 0.02 l/cm $H_2O$, which complies well with the resistance of human airways.

It should be emphasized that in the above and in the following, an air source refers to any source capable of supplying the pressure required for testing the mask seal. The air source may be a bag (sometimes called an AMBU-bag) that sucks air from the surroundings or from a reservoir, or it may be a pressure tank, the rescuer's own lungs or another suitable source.

The invention will now be explained in greater detail through examples of embodiments also illustrated in the accompanying drawings, in which.

Figure 6:
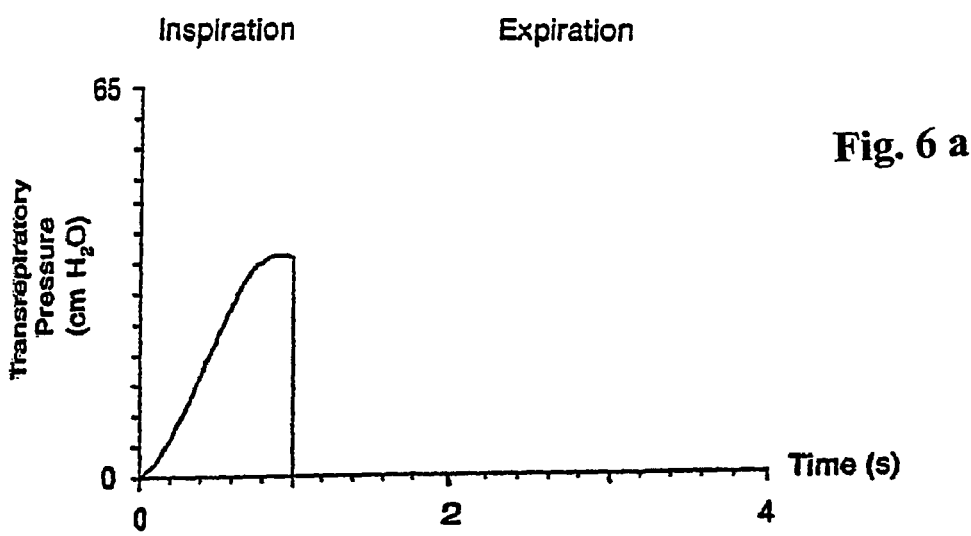
Figure 6:
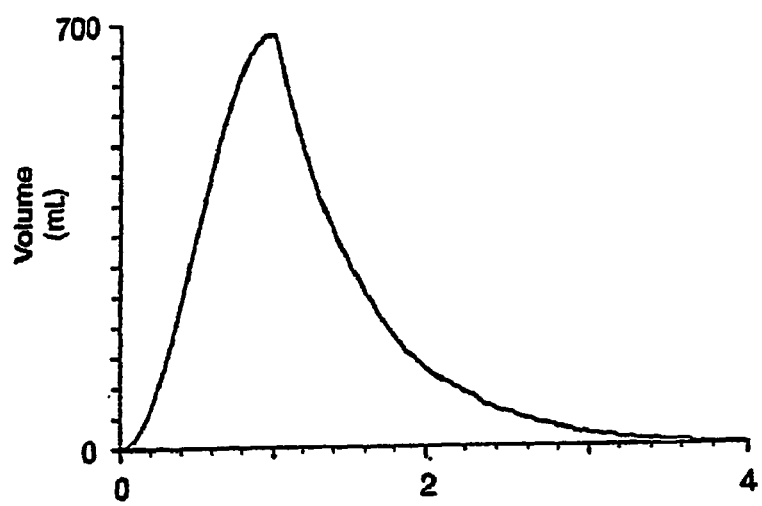
Figure 6:
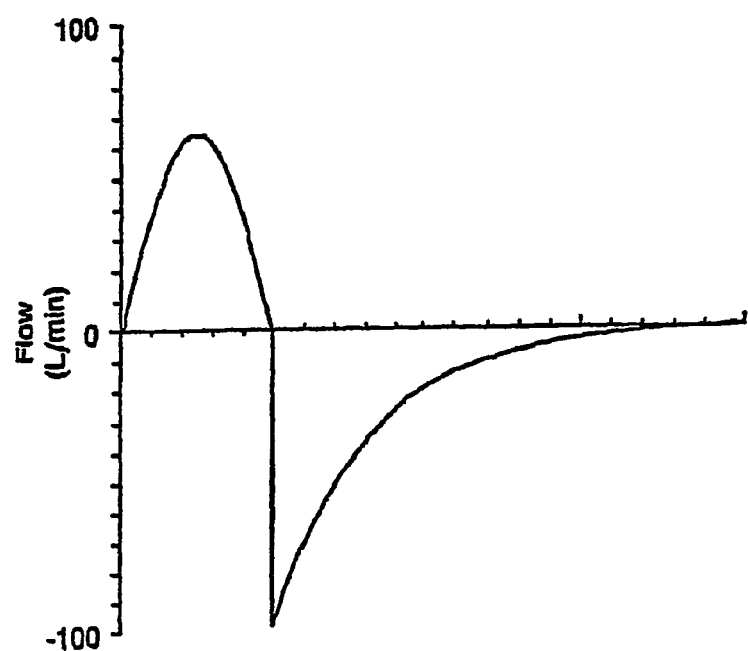

FIGS. 6a, b and c show characteristic waveforms for volume controlled ventilation of an adult human being.

Figure 1:
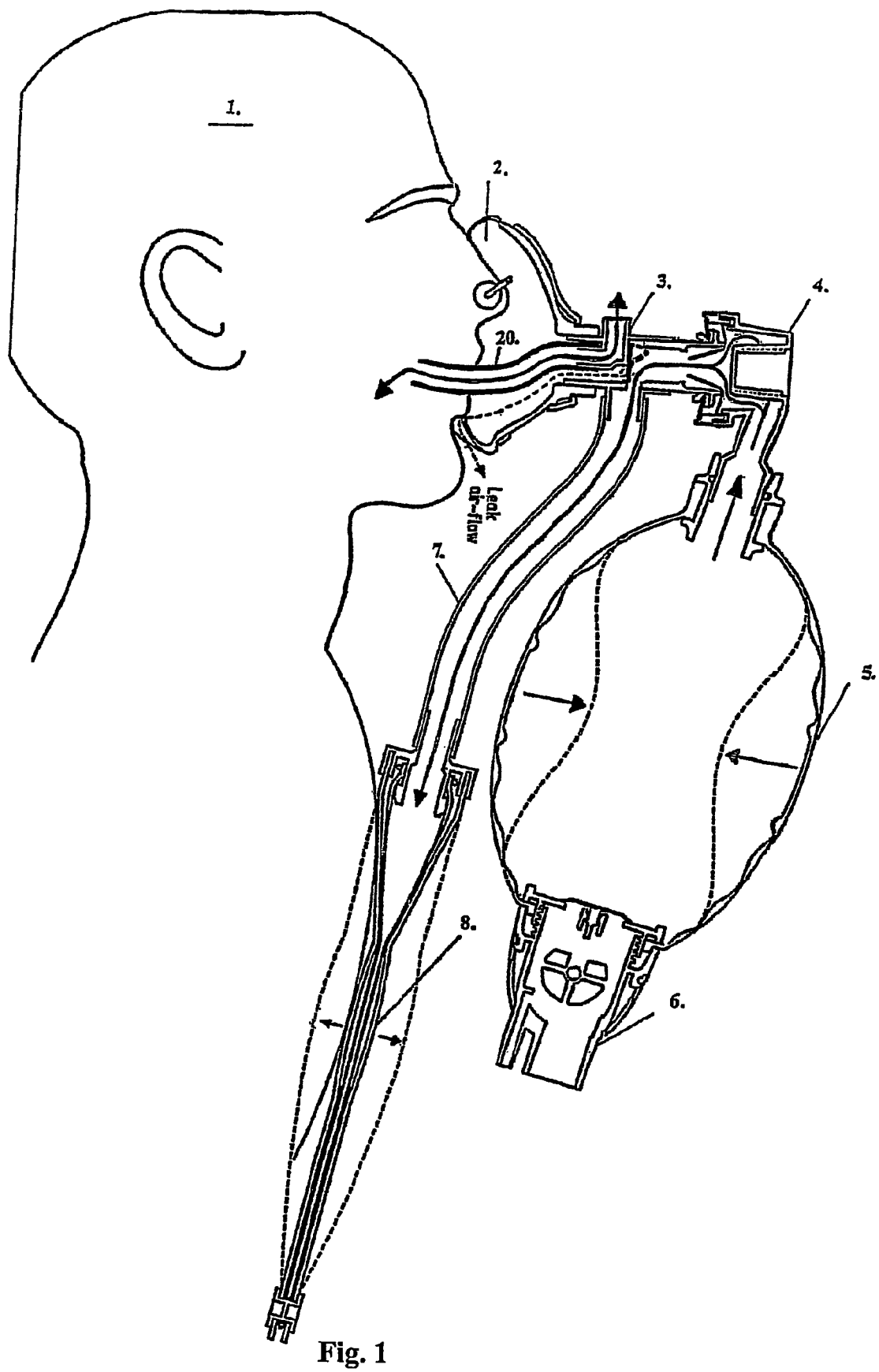
FIG. 1 is a section of an arrangement of training equipment according to the present invention for practicing breathing facilitation on breathing persons.

FIG. 1 is a sectional drawing of an arrangement of equipment used when practicing on a breathing person. A volunteer 1 is shown lying-down. A patient mask 2 having a standard 22 mm internal diameter connection is arranged over the volunteer's mouth and nose. This mask may be any type of commercially available mask, e.g. one manufactured and marketed by Laerdal Medical AS under item number 860220 or 870220.

An adapter 3 according to the invention is connected to the patient mask 2, which adapter 3 will be explained in detail hereinbelow. The adapter 3 is also connected to a patient valve 4. This may be of a type manufactured and marketed by Laerdal Medical AS under item number 851300, 851200 or 560200, or an equivalent patient valve from another manufacturer, with a nozzle with a standard 22 mm external diameter connection. As the construction and operation of such a valve will be well known to a person skilled in the art, the patient valve will not be explained in any greater detail herein. What is important to the present invention is that the patient valve is designed to admit air in the direction of the patient, and let air from the patient escape to the surroundings.

Furthermore, there is a bag 5 connected to the patient valve. This bag 5 may be of a type manufactured and marketed by Laerdal Medical AS under item number 870100, 860100 or 850100, or it may be an equivalent bag from another manufacturer. As an alternative, one can also use pumps, such as described in e.g. U.S. Pat. No. 5,217,006. It is also possible to use a gas powered regulator or, in special cases, a pressure gas cylinder or an electrical pump. However, use of a manual pump will maximise the benefit gained from the training.

At the opposite end of the bag 5 there is an intake valve 6. This may be of the type described in NO 2002 3404 or an equivalent valve. The only feature of importance to the present invention is that the intake valve 6 must be designed to admit air into the bag 5 and prevent air from flowing in the opposite direction.

To the adapter 3 there is also connected an artificial lung 8, via a hose 7. The artificial lung may be of the same type as that found in manikins, or it may be a simple bag.

Figure 2:
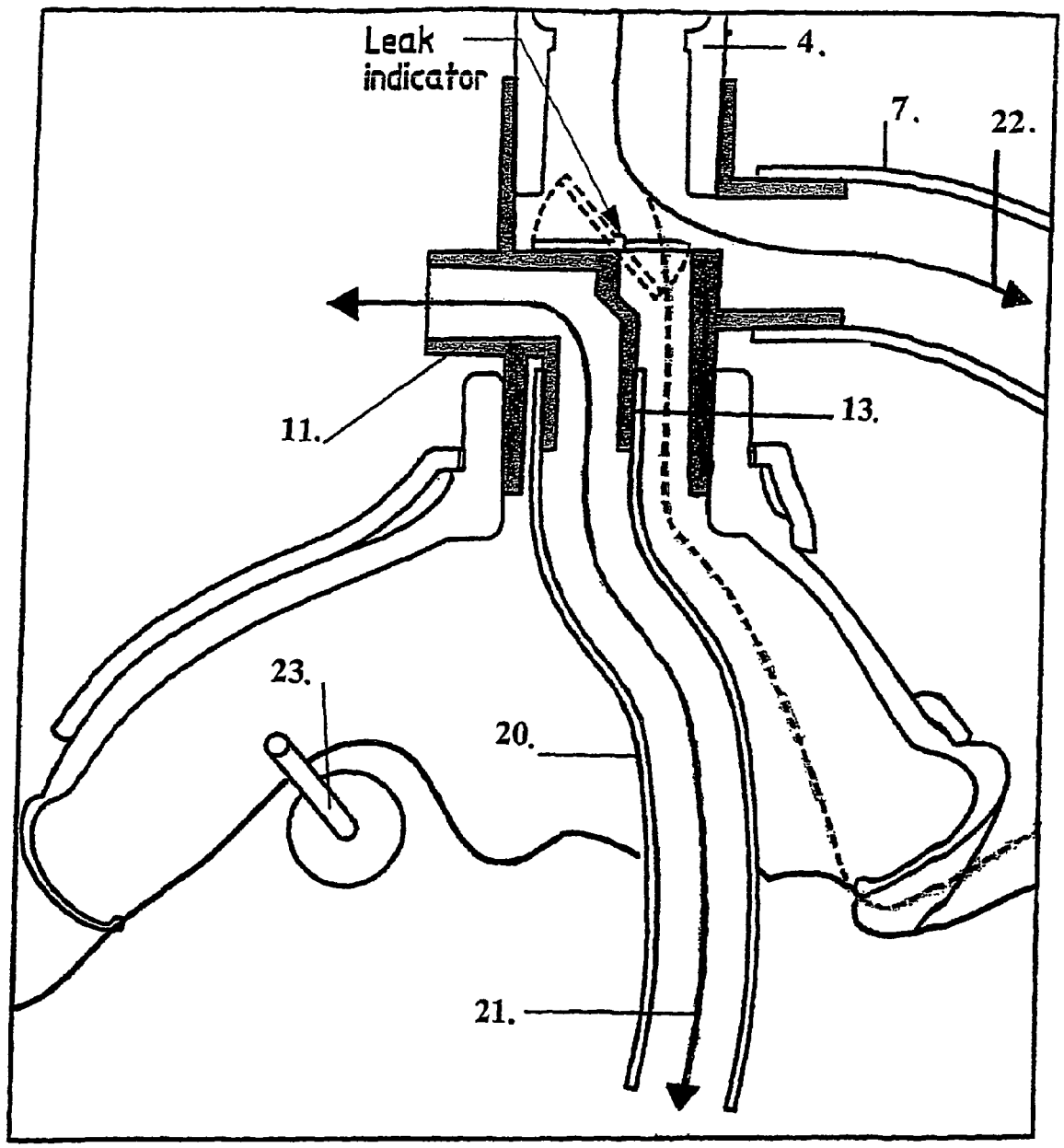
FIG. 2 shows a detail of FIG. 1.
Figure 3:
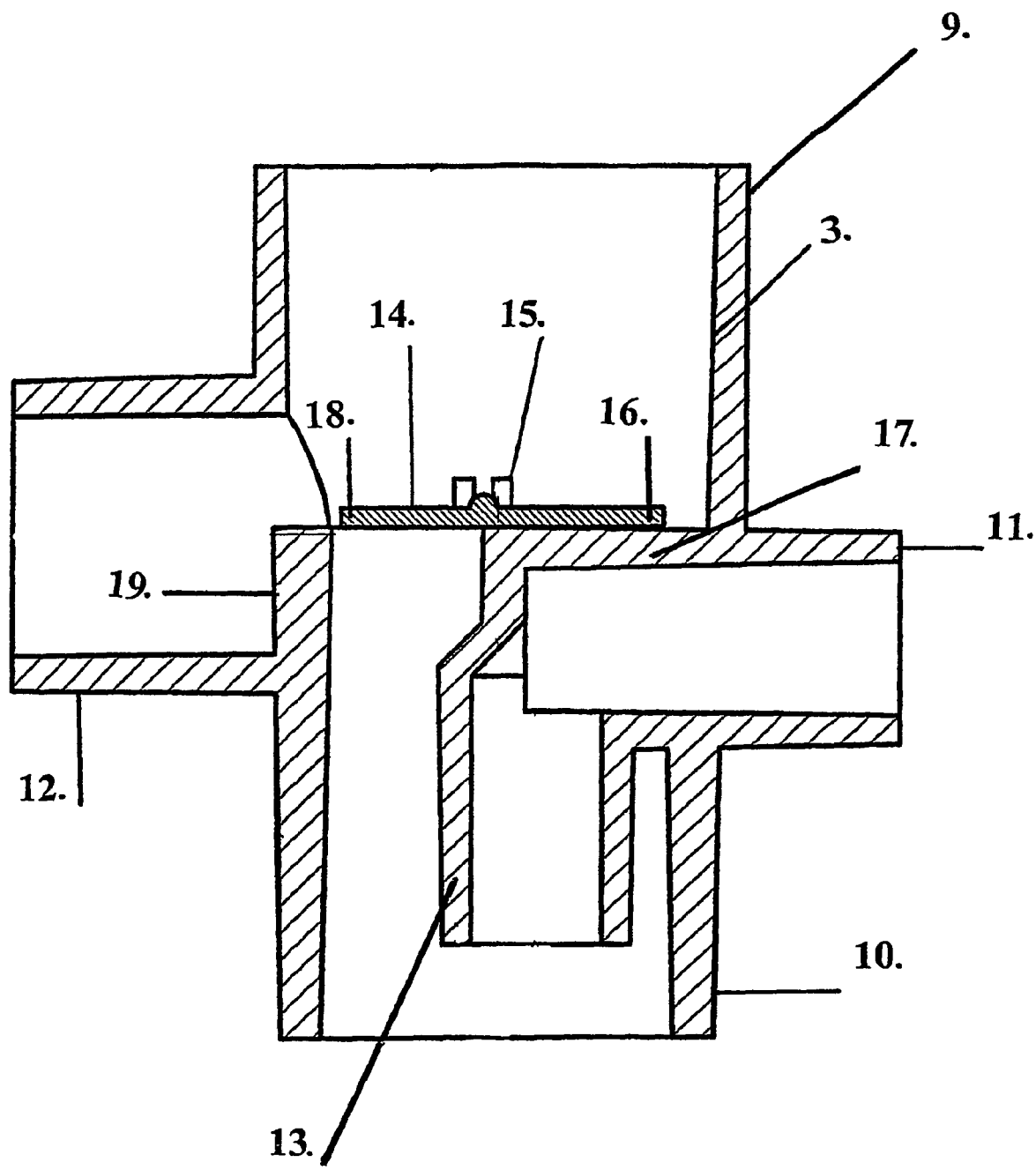
FIG. 3 shows a section through an adapter according to the invention.
Figure 4:
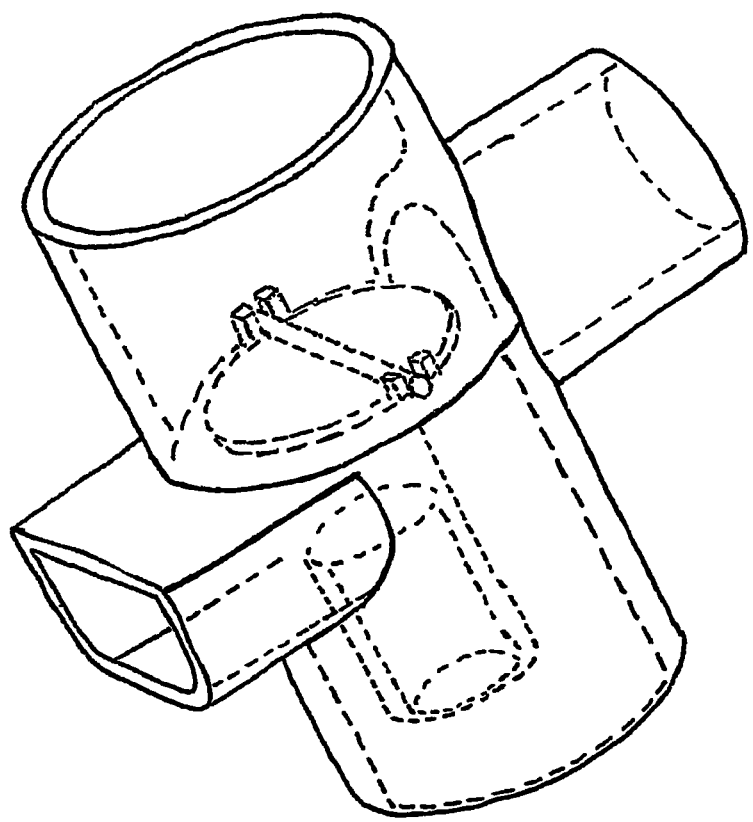
FIGS. 4a and 4b are perspective views of how the adapter of FIG. 3 works in the cases of good and poor mask seals, respectively.
Figure 4:
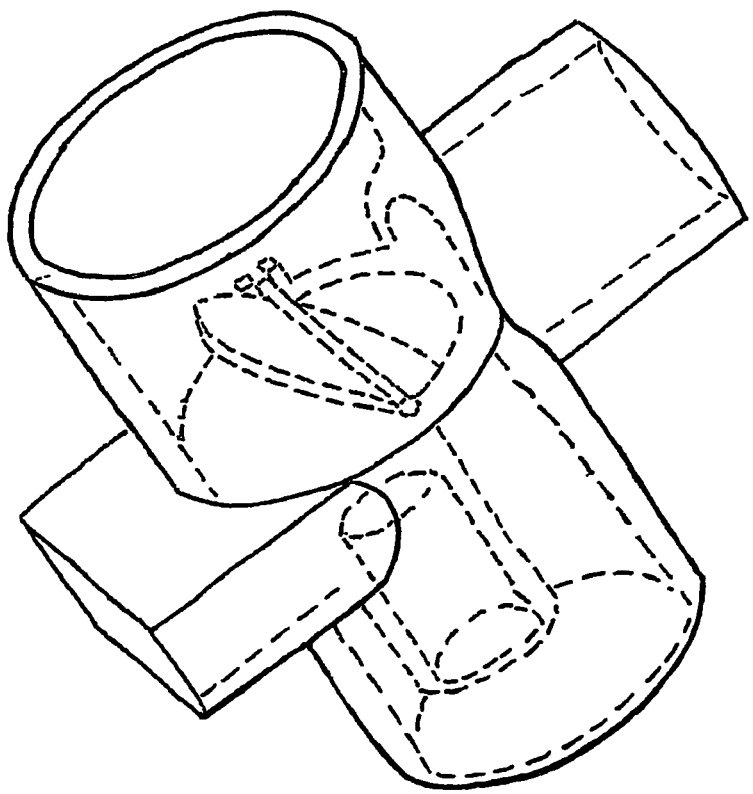

Reference is made to FIG. 3, which shows a section through the adapter 3. The adapter 3 has five connecting pipes. The first connection 9 is designed to be connected to the patient valve 4. The second connection 10 is designed to be connected to the patient mask 2. It is practical for the second connection 10 to be arranged opposite the first connection 9. The third connection 11 is designed for connection to the hose 7 that leads to the artificial lung 8. The fourth connection 12 leads to the surroundings. The fifth connection 13 is arranged inside the connection 10 and is designed to be connected to a hose 20 (see FIG. 2). The third and fifth connections 11, 13 communicate freely with each other. However there is no communication between these two connections 11, 13 and the rest of the connections. The first connection 9 communicates with the fourth connection 12 and also with the second connection 10. A damper 14 is disposed between the first and second connections 9, 10. The damper 14 is designed to tilt about a first hinge 15, between a position in which communication between the first and second connections 9, 10 is blocked, and a position at an angle to this (see FIG. 4), where there is open communication between the first and second connections 9, 10. The damper 14 has a first part 16, on one side of the hinge 15, abutting a shoulder 17 in the adapter 3 and a second part 18, on the other side of the hinge 15, outside the shoulder 17. The first part 16 of the damper 14 is heavier than the second part of the damper 14, giving it a neutral position such as that shown in FIG. 3.

A half wall 19 covers that part of the bore of the fourth connection 12 located below (according to the orientation of FIG. 3) the damper 14 in its neutral position, preventing air from flowing past the damper 14 via the fourth connection 12.

In accordance with the above, a first passage is formed between the first connection 9 and the second connection 10, a second passage between the first connection 9 and the fourth connection 12, and a third passage between the third connection 11 and the fifth connection 13.

Reference is now made to the detail section in FIG. 2. As shown, there is a hose 20 running from the volunteer's 1 mouth to the fifth connection 13, thereby allowing the volunteer to breathe through the mouth and exchange air with the surroundings via the hose 20 and the third passage in the adapter 3, as indicated by the double arrow 21.

When the rescuer squeezes the bag 5 air is forced via the patient valve 4, through the second passage of the adapter 3, out into the hose 7 and on to the artificial lung 8, as indicated by arrow 22. The artificial lung 8 is constructed so as to ensure that the introduction of air will result in a visible raising of the lung 8. Moreover, the lung provides a certain amount of resistance, providing an imitation of the sensation of ventilating a human lung. The return air from the lung flows back the same way and out to the surroundings via a port on the patient valve. The lung 8 provides an indication of how good the mask seal is, and also of how good the bagging volume is.

In the course of this operation, an excess pressure will build up on the inside of the patient mask 2. In order to prevent air from being forced down through the volunteer's respiratory passage via the nose, the volunteer may be provided with a nose clip 23.

If the mask seal is poor, the excess pressure inside the patient mask 2 will escape between the mask and the volunteer's face. Some of the air flowing in through the first connection 9 on the adapter 3 will then flow through the first passage to the inside of the mask. This leakage will result in the artificial lung 8 not lifting sufficiently, and the resistance felt by the rescuer during the compression of the bag 5 will be less.

The purpose of the damper 14 is to act as an additional leakage indicator, and it has no functional significance beyond this. FIGS. 4a and 4b illustrate this function. Preferably the adapter 3 made from a transparent material, making the damper 14 visible. If the air flows only through the third passage and out into the lung 8, the damper will be horizontal (i.e. abutting the shoulder 17), as shown in FIG. 4a. If the mask seal deteriorates, letting some of the air flow through the first passage, the damper will tilt in the air flow, to a position as shown in FIG. 4b, thereby allowing the user to quickly notice the leakage flow through the first passage.

Instead of an artificial lung, it is also possible to arrange a restriction at the fourth connection 12 to offer a certain amount of resistance in order to create an illusion of the resistance and back pressure in a human lung.

The above illustrates the fact that, to a great extent, it is possible to use existing components. The patient mask, the patient valve, the bag and the intake valve can be the same components as those used in real patient treatment. The hoses 7 and 20 can be made from standard hose materials, and the lung 8 can be one of several used in manikins today. Thus only the adapter 3 is specially made for this training purpose. Furthermore it is possible to convert the equipment into ordinary patient treatment equipment just by removing the adapter 3 with the hoses 7 and 20, and connecting the patient valve 4 directly to the patient mask 2.

When using the training equipment shown in FIG. 1, only the hose 7 and the adapter 3 will be contaminated. For that reason, these components can be disposable or constructed in a way which allows them to be cleaned after use. The remaining components will not require cleaning prior to being used on the next volunteer. It is also possible to introduce an air filter into the system in order to reduce the number of components exposed to contamination.

Still, it is also possible to envisage the adapter being constructed as an integral part of the patient mask and/or the patient valve.

The adapter 3 and the hose 20 may also be manufactured all in one piece.

In a further alternative embodiment the connecting pipes that form the third passage and the hose may be constructed as a first unit (snorkel), and the connecting pipes that form the second passage may be constructed as a second unit. These two units can be assembled to act as the adapter 3. The advantage of this is that only the first unit will be contaminated after use. This unit is somewhat simpler than the adapter 3 and may therefore be slightly cheaper. The drawback is that the assembly becomes a little more complex. In a simple embodiment of the invention it is also possible to use only the first unit (the snorkel), as air forced into the mask has no outlet. This will work well for testing the mask seal but will not allow any checking of the delivered volume.

Instead of a lung 8, use may be made of a volume indicator, e.g. an electronic volume indicator.

In a simplified embodiment of the present invention, there is provided a snorkel that extends through the mask to the volunteer's mouth and/or nose. The snorkel may be a hose passed through a hole in the mask, or it may be an integral part of the mask.

Figure 5:
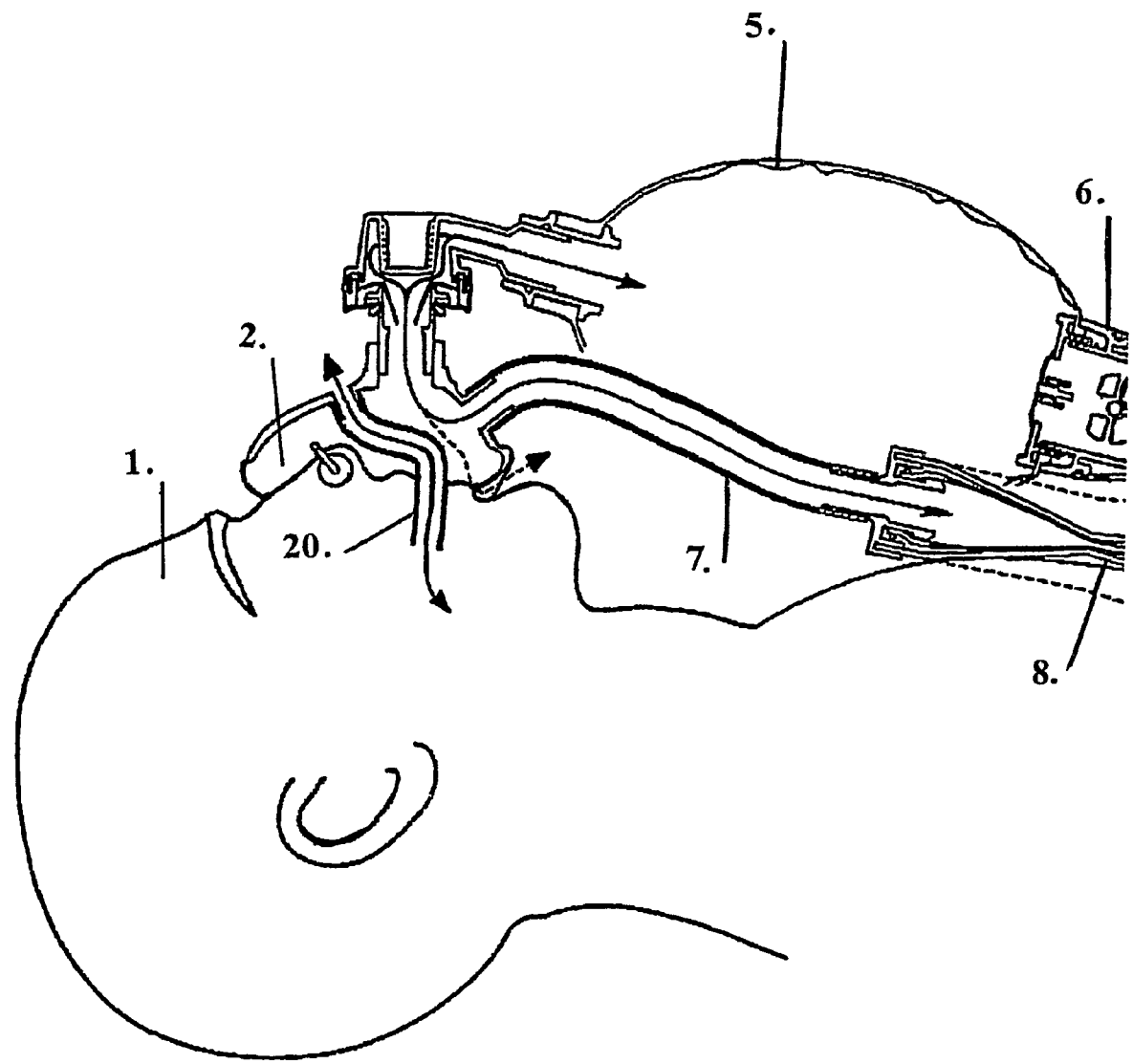
FIG. 5 illustrates an alternative embodiment of the invention.

A conceivable alternative would be to make a special training mask, as illustrated in FIG. 5, the mask comprising communication with an artificial lung. Thus in practice, the artificial lung, which is the same as a back pressure device, is located in an extension of the passage from the air source to the face mask. This obviates the need for a connecting link between the patient valve on the bag and the patient mask; instead use is made of a separate training mask. This training mask may also have a separate passage for allowing the volunteer to breathe freely to the surroundings, either via a connection through the sidewall of the mask or by separate communication up through the mask connecting pipe.

FIGS. 6a, b and c show characteristic waveforms for volume controlled ventilation of an adult human being. FIG. 6a shows transrespiratory pressure in cm $H_2O$ over a period in time in seconds. As the graph shows, during the inspiration phase, which lasts for about one second, the pressure increases from zero to about 36 centimeter $H_2O$, after which the pressure is immediately released to allow the lungs to expire. FIG. 6b shoes the volume administered in milliliters. During the inspiration phase the volume increases from zero to about 700 ml over the same period of one second, after which the pressure is released and the volume is expired over a period of about 3 seconds.

FIG. 6c shows the flow into and out of the lungs in liters per minute. The flow increases from zero to about 65 l/min over a period of about 0.5 second and then decreases to zero again over the next 0.5 second. When the pressure is releases the flow increases again, but in the opposite direction and abruptly to a maximum of about 100 1/min to gradually decrease to zero over the next 3 seconds.

The volume and the flow is controlled by the rescuer, e.g. by his or her hand squeezing of a bag. If the rescuer manage to empty the bag sufficiently he or she will have administered about 700 to 1000 ml air (in the case of a bag for adults and no additional oxygen supply). In the case of additional oxygen supply the total administered volume should be limited to about 400 to 600 ml. The administration of this air/oxygen should take about 1 second.

With a back pressure device according to the present invention the pressure should increase while the air/oxygen is administered, to create a close to real life experience for the rescuer. The resistance should be within the range of 5-40 cm $H_2O$/liter/second. A typical healthy adult airway has a resistance of about 20 cm $H_2O$/liter/second. Consequently the back pressure device should be calibrated to approximately this resistance. However, the back pressure device may preferably have the option of adjustment of the resistance, e.g., to simulate asthma, which results in a greater resistance than a healthy lung. The adjustable back pressure device may be achieved, e.g., by an adjustable restriction. The means for providing this are readily available to a person of skill.

A lung of a human being also has typically a compliance of about 0.02 liter/cm $H_2O$. The compliance maybe adjustable within the range of 0.01 to 0.15 liter/cm $H_2O$. This provides for simulation of, e.g., COAD (Chronic obstructive airways disease), which results in very stiff lungs. The adjustable compliance may be achieved, e.g., by a test lung having elastic means that may be varied in length or in number. These means are readily available to a person of skill.

The invention claimed is:

1. A device for practicing mask ventilation comprising:
   a patient mask having a seal for contacting a face of a person, the mask adapted to be placed over the nose and mouth of the person, the mask having an interior and an aperture between the interior and the surroundings;
   an adaptor sized to fit within the aperture of the mask, the adaptor having
      a first passage for providing fluid communication between the mask interior and a source of air, and
      a second passage for providing fluid communication between the source of air and a back pressure device;

wherein air flowing from the source of air through the first passage and into the mask interior contacts the seal, and is used to determine if the mask is sealed to the face of the person.

2. A device according to claim 1, wherein it further comprises a third passage for providing fluid communication between the person and the surroundings, thereby allowing the person to breathe.

3. A device according to claim 1, wherein said first passage includes an indicator to indicate air flow through said first passage.

4. A device according to claim 3, wherein said indicator is a damper biased in a crosswise position in said first passage.

5. A device according to claim 1, further comprising the back pressure device defined as an artificial lung, which upon filling will indicate the volume delivered from said air source.

6. A device according to claim 1, further comprising the back pressure device defined as a restriction.

7. A device according to claim 5, wherein the resistance provided by the back pressure device is between 5 and 40 cm H2O/l/s.

8. A device according to claim 5, wherein the resistance provided by the back pressure means is about 20 cm H2O/l/s.

9. A device according to claim 5, wherein said back pressure device has a compliance simulating the compliance of a human airway.

10. A device according to claim 5, wherein the back pressure device has a compliance between 0.01 and 0.15 l/cm H2O.

11. A device according to claim 5, wherein the back pressure device has a compliance of about 0.02 l/cm H2O.

12. A device according to claim 2, wherein said first, second and third passages are formed in the adaptor.

13. A device according to claim 2, wherein said third passage is formed in a separate unit.

14. A device according to claim 13, wherein said third passage extends through the wall of the mask at a distance from the first and second passage.

15. A device according to claim 2, wherein said third passage communicates with both the person's mouth and nose.

16. The device of claim 1 wherein the first passage is in fluid communication with the second passage; and the device further comprising a damper oriented within the adaptor by a hinge, the damper for controlling air flow to the mask interior, the damper having a first part and a second part arranged on either side of the hinge;

wherein the first part of the damper is heavier than the second part, such that the first part of the hinge causes it to bias to a closed position to prevent air flow through the second passage, the damper opening due to a pressure difference between the first passageway and the second passageway, the pressure difference indicating a leak across the seal from the interior of the mask to the surroundings.

17. An adaptor for use with a patient mask having a seal for contacting a face of a person, the mask having an interior portion and an aperture between the interior portion and the surroundings, the adaptor for practicing mask ventilation, the adaptor comprising:

a first passage adapted to allow air flow between an air source and a back pressure device;

a second passage adapted to allow air flow between the first passage and an interior portion of a mask, a damper oriented in the second passage for controlling air flow from the first passage to the second passage; and a third passage adapted to allow air flow between a mouth of a person wearing the mask and the surroundings, thereby allowing the person to breathe.

18. The adaptor of claim 17, wherein the damper has a first part and a second part arranged on either side of a hinge, the first part of the damper heavier than the second part, such that the first part of the hinge causes it to bias to a closed position preventing air flow through the second passage, the damper opening due to a pressure difference between the first passageway and the second passageway, the pressure difference indicating a leak across the seal from the interior portion of the mask to the surroundings.

* * * * *